(12) United States Patent
Kyoi

(10) Patent No.: US 8,394,793 B2
(45) Date of Patent: Mar. 12, 2013

(54) THERAPEUTIC AGENT FOR INFLAMMATORY BOWEL DISEASE

(75) Inventor: Takashi Kyoi, Kyoto (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 223 days.

(21) Appl. No.: 13/000,791

(22) PCT Filed: Jun. 22, 2009

(86) PCT No.: PCT/JP2009/061287
§ 371 (c)(1),
(2), (4) Date: Dec. 22, 2010

(87) PCT Pub. No.: WO2009/157398
PCT Pub. Date: Dec. 30, 2009

(65) Prior Publication Data
US 2011/0118254 A1    May 19, 2011

(30) Foreign Application Priority Data
Jun. 23, 2008    (JP) .................................. 2008-162640

(51) Int. Cl.
*A61K 31/4965*    (2006.01)
*A61K 31/5375*    (2006.01)
(52) U.S. Cl. .................................. 514/231.2; 514/252.1
(58) Field of Classification Search ................ 514/231.2, 514/252.1
See application file for complete search history.

(56) References Cited

U.S. PATENT DOCUMENTS
2004/0102436 A1    5/2004    Asaki et al.

FOREIGN PATENT DOCUMENTS
| JP | 10-194992 A1 | 7/1998 |
| WO | 2006/055481 A1 | 5/2006 |
| WO | 2006/058080 A1 | 6/2006 |

OTHER PUBLICATIONS

Tamaki Yamada, et al., A Comparative Analysis of Two Models of Colitis in Rats, Gastroenterology, 1992, 102, pp. 1524-1534.

Mitsuaki Okayama, et al., Aggravation by Selective COX-1 and COX-2 Inhibitors of Dextran Sulfate Sodium (DSS)—Induced Colon Lesions in Rats, Dig Dis Sci, 2007, 52, pp. 2095-2103.

Yuka Ikenoue, et al., Development and validation of a novel IL-10 deficient cell transfer model for colitis, International Immunopharmacology, 5, 2005, pp. 993-1006.

Jun Sato, et al., Effect of Mesalazine in Rat Models of Inflammatory Bowel Disease, Jpn Pharmacol Ther, vol. 36, No. 4, 2008, pp. 293-301.

PCT International Preliminary Report on Patentability for PCT/JP2009/061287 issued on Feb. 8, 2011.

*Primary Examiner* — Jennifer M Kim
(74) *Attorney, Agent, or Firm* — McDermott Will & Emery LLP

(57) ABSTRACT

The main object of the present invention is to provide an agent for the treatment of inflammatory bowel diseases.

The present invention relates to an agent for the treatment of inflammatory bowel diseases containing the heterocyclic derivative represented by the following general formula (1) or a pharmaceutically acceptable salt thereof as an active ingredient;

[chem. 1]

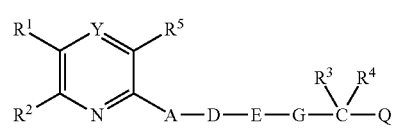

(1)

In the formula (1),
$R^1$ and $R^2$ are the same or different and each represents an optionally substituted aryl;
$R^3$ and $R^4$ are the same or different and each represents hydrogen atom or alkyl;
$R^5$ represents hydrogen atom, alkyl or halogen atom;
Y represents N or N→O;
A represents $NR^6$, and $R^6$ represents hydrogen atom, alkyl, etc.;
D represents alkylene or alkenylene which is optionally substituted with hydroxy;
E represents phenylene or a single bond;
G represents O, S, etc.; and
Q represents carboxy, alkoxycarbonyl, etc.

2 Claims, 1 Drawing Sheet

THERAPEUTIC AGENT FOR INFLAMMATORY BOWEL DISEASE

CROSS REFERENCE TO PRIOR APPLICATIONS

This application is a U.S. National Phase application under 35 U.S.C. §371 of International Application No. PCT/JP2009/061287, filed on Jun. 22, 2009 and claims benefit of priority to Japanese Pat. Application No. 2008-162640, filed on Jun. 23, 2008. The International Application was published in Japanese on Dec. 30, 2009 as WO 2009/157398 A1 under PCT Article 21(2). The contents of these applications are hereby incorporated by reference.

TECHNICAL FIELD

The present invention relates to an agent for treatment of inflammatory bowel diseases containing a heterocyclic derivative (hereinafter, referred to as "the present heterocyclic derivative (1)") represented by the following general formula (1) or a pharmaceutically acceptable salt thereof as an active ingredient;

[chem. 1]

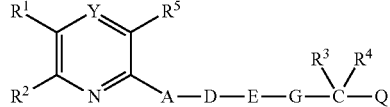

(1)

In the formula (1), $R^1$ and $R^2$ are the same or different and each represents an optionally substituted aryl, and the substituents are the same or different and one to three substituents are selected from the group consisting of halogen atom, alkyl, haloalkyl, arylalkyl, alkoxy, alkylthio, alkoxyalkyl, alkylsulfonyl, hydroxy, amino, monoalkylamino, dialkylamino, carboxy, cyano and nitro;

$R^3$ and $R^4$ are the same or different and each represents hydrogen atom or alkyl;

$R^5$ represents hydrogen atom, alkyl or halogen atom;

Y represents N or N→O;

A represents $NR^6$, and $R^6$ represents hydrogen atom, alkyl, alkenyl or cycloalkyl;

D represents alkylene or alkenylene which is optionally substituted with hydroxy, or A and D are combined with each other to form a divalent group represented by the following formula (2)

[chem. 2]

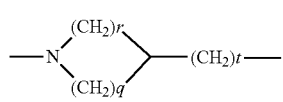

(2)

[In the formula (2), r represents an integer of 0 to 2, q represents 2 or 3 and t represents an integer of 0 to 4.];

E represents phenylene or a single bond, or D and E are combined with each other to form a divalent group represented by the following formula (3)

[chem. 3]

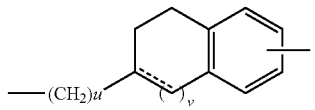

(3)

( represents a single bond or a double bond.)

[In the formula (3), u represents an integer of 0 to 2 and v represents 0 or 1.];

G represents O, S, SO or $SO_2$; and

Q represents carboxy, alkoxycarbonyl, tetrazolyl, carbamoyl, monoalkylcarbamoyl, dialkylcarbamoyl or the group represented by the following formula (4).

[chem. 4]

$$-CONH-SO_2-R^7 \qquad (4)$$

[In the formula (4), $R^7$ represents amino, monoalkylamino, dialkylamino, hydroxy, any of the group of the following 1) to 4) which are optionally substituted with 1 to 3 substituents selected from the group consisting of halogen atom, alkyl, haloalkyl, arylalkyl, alkoxy, alkylthio, alkoxyalkyl, alkylsulfonyl, hydroxy, amino, monoalkylamino, dialkylamino, carboxy, cyano and nitro;

1) alkyl,
2) aryl,
3) aryloxy, and
4) heterocyclic group.]

BACKGROUND ART

Inflammatory bowel disease (IBD) is a common name for the diseases of unknown cause represented by ulcerative colitis and Crohn's disease where chronic inflammation and/or ulcer are/is induced in the large and small intestinal mucosa. Many of the patients develop the disease in relatively young age between teens to twenties showing clinical symptoms such as diarrhea, fever or abdominal pain or systemic inflammatory symptoms and it has been a problem that not only nutrition of food/beverage orally ingested is unable to be efficiently absorbed but also social life is deteriorated due to dietary restrictions and frequent evacuations. As to the cause for the inflammatory bowel diseases, abnormal autoimmune and enterobacteria have been reported but the cause has not been clarified yet and it is the current status that no therapeutic means resulting in complete cure has been found yet.

As to the treatment for inflammatory bowel diseases such as ulcerative colitis, a drug therapy using salazosulfapyridine, 5-aminosalicylic acid, steroids or immunosuppressants or a dietary therapy has been carried out already. However, no sufficient therapeutic effect is achieved by that and, moreover, in steroids and immunosuppressants, side effects due to a long-term administration are becoming a big problem.

On the other hand, the present heterocyclic derivative (1) or a pharmaceutically acceptable salt thereof has already been reported to be useful for the treatment of pulmonary hypertension or obstructive arteriosclerosis as a $PGI_2$ receptor agonist (see, for example, Patent Document 1).

Patent Document 1: Pamphlet of International Publication WO 02/088084

DISCLOSURE OF THE INVENTION

Problems that the Invention is to Solve

The main object of the present invention is to provide a novel agent for the treatment of inflammatory bowel diseases.

Means for Solving the Problems

The present inventor has found that the present heterocyclic derivative (1) has a therapeutic effect for colitis resulted by administration of an aqueous solution of dextran sulfate in rats and has achieved the present invention.

An example of the present invention is an agent for the treatment of inflammatory bowel diseases containing the present heterocyclic derivative (1) or a pharmaceutically acceptable salt thereof as an active ingredient.

BRIEF DESCRIPTION OF THE DRAWINGS

In FIG. 2, triangular mark shows the control group and square mark shows the group administered with 2-{4-[N-(5,6-diphenylpyrazin-2-yl)-N-isopropylamino]butyl-oxy}-N-(methylsulfonyl)acetamide (hereinafter, referred to as "the compound A").

BEST MODE FOR CARRYING OUT THE INVENTION

Figure 1:
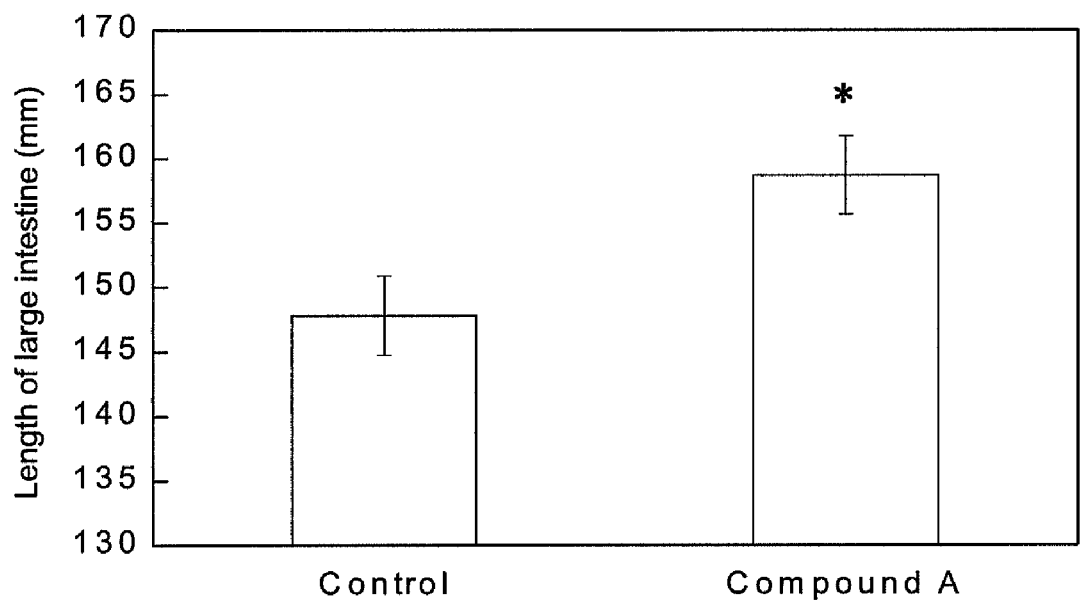
FIG. 1 shows a inhibitory effect on shrinkage of large intestine. An ordinate represents the length (mm) of the large intestine.

In the present heterocyclic derivative (1), the preferred one is that where $R^1$ and $R^2$ are the same or different and each represents optionally substituted phenyl, and the substituents are the same or different and one to three substituents selected from the group consisting of halogen atom, alkyl and alkoxy;

$R^3$ and $R^4$ are the same or different and each represents hydrogen atom or alkyl;

$R^5$ represents hydrogen atom;

Y represents N;

A represents $NR^6$, and $R^6$ represents alkyl;

D represents alkylene;

E represents a single bond;

G represents O; and

Q represents carboxy or a group represented by the following formula (4), and $R^7$ represents amino, monoalkylamino, dialkylamino, hydroxy, or any of the group of the following 1) to 4) which are optionally substituted with 1 to 3 substituents selected from the group consisting of halogen atom, alkyl, haloalkyl, arylalkyl, alkoxy, alkylthio, alkoxyalkyl, alkylsulfonyl, hydroxy, amino, monoalkylamino, dialkylamino, carboxy, cyano and nitro;

1) alkyl,
2) aryl,
3) aryloxy, and
4) heterocyclic group.

To be more specific, the compound A and 2-{4-[N-(5,6-diphenyl-pyrazin-2-yl)-N-isopropylamino]butyloxy}acetic acid (hereinafter, referred to as "the compound B") are preferable for example.

As to the "alkyl" in the present invention, that which is straight or branched having 1 to 6 carbon atoms, for example, methyl, ethyl, n-propyl, isopropyl, n-butyl, isobutyl, sec-butyl, tert-butyl, n-pentyl, isopentyl, n-hexyl or isohexyl may be exemplified. Particularly, alkyl having 1 to 4 carbon atoms is preferable.

As to an alkyl moiety in "haloalkyl", "arylalkyl", "alkylthio", "alkoxyalkyl", "alkylsulfonyl", "monoalkylamino", "dialkylamino", "monoalkylcarbazoyl" and "dialkylcarbamoyl" in the present invention, that which is the same as the already-mentioned alkyl may be exemplified.

As to the "alkoxy" in the present invention, that which is straight or branched having 1 to 6 carbon atoms, for example, methoxy, ethoxy, n-propoxy, isopropoxy, n-butoxy, isobutoxy, sec-butoxy, tert-butoxy, n-pentyloxy, isopentyloxy, n-hexyloxy or isohexyloxy may be exemplified. Particularly, alkoxy having 1 to 4 carbon atoms is preferable.

As to an alkoxy moiety in "alkoxycarbonyl" and "alkoxyalkyl" in the present invention, that which is the same as the already-mentioned alkoxy may be exemplified.

As to the "alkenyl" in the present invention, that which is straight or branched having 2 to 6 carbon atoms, for example, vinyl, 1-propenyl, 2-propenyl, 1-butenyl, 2-butenyl, 3-butenyl, 1-pentenyl, 2-pentenyl, 3-pentenyl, 4-pentenyl, 4-methyl-3-pentenyl, 1-hexenyl, 2-hexenyl, 3-hexenyl, 4-henexyl or 5-hexenyl may be exemplified. Particularly, alkenyl having 3 or 4 carbon atoms is preferable.

As to the "cycloalkyl" in the present invention, that which has 3 to 8 carbon atoms, for example, cyclopropyl, cyclobutyl, cyclopentyl, cyclohexyl, cycloheptyl or cyclooctyl may be exemplified. Particularly, cycloalkyo having 5 to 7 carbon atoms is preferable.

As to the "halogen atom" in the present invention, fluorine atom, chlorine atom, bromine atom and iodine atom may be exemplified.

As to the "aryl" in the present invention, that which has 6 to 10 carbon atoms, for example, phenyl, 1-naphthyl or 2-naphthyl may be exemplified. Particularly, phenyl is preferable.

As to the aryl moiety in "arylalkyl" and "aryloxy" in the present invention, that which is the same as in the already-mentioned aryl may be exemplified.

As to the "alkylene" in the present invention, that which is straight or branched having 1 to 8 carbon atoms, for example, methylene, ethylene, 1-methylethylene, 2-methylethylene, trimethylene, tetramethylene, pentamethylene, hexamethylene, heptamethylene or octamethylene may be exemplified. Particularly, alkylene having 3 to 6 carbon atoms is preferable, and alkylene having 4 carbon atoms is more preferable.

As to the "alkenylene" in the present invention, that which is straigh or branched having 2 to 8 carbon atoms, for example, ethenylene, 1-propenylene, 2-propenylene, 1-butenylene, 2-butenylene, 3-butenylene, 1-pentenylene, 2-pentenylene, 3-pentenylene, 4-pentenylene, 4-methyl-3-pentenylene, 1-hexenylene, 2-hexenylene, 3-hexenylene, 4-hexenylene, 5-hexenylene, 1-heptenylene, 2-heptenylene, 3-heptenylene, 4-heptenylene, 5-heptenylene, 6-heptenylene, 1-octenylene, 2-octenylene, 3-octenylene, 4-octenylene, 5-octenylene, 6-octenylene or 7-octenylene may be exemplified. Particularly, alkenylene having 3 to 6 carbon atoms is preferable, and alkenylene having 4 carbon atoms is more preferable.

As to the "heterocyclic group" in the present invention, the following (1) or (2) may be exemplified.

(1) A five- to six-membered aromatic ring group having 1 to 4 hetero atoms selected from nitrogen atom, oxygen atom and sulfur atom, or a benzene condensed ring thereof and nitrogen atom and sulfur atom may form an oxide when a ring-constituent atom is nitrogen atom or sulfur atom. Examples thereof include 1-pyrrolyl, 2-pyrrolyl, 3-pyrrolyl, 3-indolyl, 2-furanyl, 3-furanyl, 3-benzofuranyl, 2-thienyl, 3-thienyl, 3-benzothienyl, 1,3-oxazol-2-yl, 4-isoxazolyl, 2-thiazolyl, 5-thiazolyl, 2-benzothiazolyl, 1-imidazolyl, 2-imidazolyl, 4-imidazolyl, 2-benzimidaolyl, 1H-1,2,4-triazol-1-yl, 1H-tetrazol-5-yl, 2H-tetrazol-5-yl, 2-pyridyl, 3-pyridyl, 4-pyridyl, 3-pyrazolyl, 2-pyrimidinyl, 4-pyrimidinyl, 2-pyrazinyl, and 1,3,5-triazin-2-yl.

(2) A four- to eight-membered saturated ring group which optionally has one to four same or different nitrogen atom, oxygen atom or sulfur atom, or a benzene condensed ring thereof, and nitrogen atom and sulfur atom may form an oxide when a ring-constituent atom is nitrogen atom or sulfur atom. Examples thereof include piperidino, piperazinyl, 3-methylpiperazin-1-yl, homopiperazinyl, morpholino, thiomorpholino, 1-pyrrolidinyl, 2-pyrrolidinyl and 2-tetrahydrofuranyl.

The present heterocyclic derivative (1) is able to be synthesized by the process mentioned in the above-mentioned Patent Document 1 (pamphlet of International Publication WO 02/088084).

Although the present heterocyclic derivative (1) may be used as a pharmaceutical just in a form of free base or acid, it is also possible to use by making into a form of a pharmaceutically acceptable salt by a known method.

Examples of the "salt" when the present heterocyclic derivative (1) shows basicity include a salt with inorganic acid such as hydrochloric acid, sulfuric acid, nitric acid, phosphoric acid, hydrofluoric acid or hydrobromic acid and with organic acid such as acetic acid, tartaric acid, lactic acid, citric acid, fumaric acid, maleic acid, succinic acid, methanesulfonic acid, ethanesulfonic acid, benzenesulfonic acid, p-toluenesulfonic acid, naphthalenesulfonic acid or camphorsulfonic acid.

Examples of the "salt" when the present heterocyclic derivative (1) shows acidity include alkali metal salt such as sodium salt or potassium salt and alkali earth metal salt such as calcium salt.

There are geometrical isomers (Z and E substances) in the present heterocyclic derivative (1) and each of the geometrical isomers and a mixture thereof are also included in the present heterocyclic derivative (1). Some of the present heterocyclic derivative (1) has asymmetric carbon(s) and each of optical isomers and racemic substance thereof are also included in the present heterocyclic derivative (1). An optical isomer is able to be produced by subjecting the racemic substance prepared as above to an optical resolution by a known method using an optically active acid (such as tartaric acid, benzoyltartaric acid, mandelic acid or 10-camphorsulfonic acid) utilizing the basicity or by using a previously-prepared optically active compound as a material.

Examples of the inflammatory bowel diseases of the present invention are ulcerative colitis, Crohn's disease, intestinal tuberculosis, ischemic colitis and intestinal ulcer associated with Behcet disease.

The agent for the treatment of inflammatory bowel diseases of the present invention is the present heterocyclic derivative (1) as it is or is the agent containing the derivative in a pharmaceutically acceptable, nontoxic and inert carrier at a rate ranging from 0.01 to 99.5% or, preferably, ranging from 0.5 to 90%.

Examples of the carrier include solid, semi-solid or liquid diluent, filler and other auxiliary agents for pharmaceutical formulation. These can be used alone or as a mixture of two or more thereof.

The agent for the treatment of inflammatory bowel diseases of the present invention may be in any of the forms of oral preparations such as powder, capsules, tablets, sugar-coated tablets, granules, diluted powder, suspension, liquid, syrup, elixir or troche and parenteral preparations such as injection or suppository in a solid or liquid dose unit. It may also be in a form of a sustained release preparation. Among them, oral preparations such as tablets are particularly preferred.

Powder is able to be manufactured by making the present heterocyclic derivative (1) into an appropriate fine size.

Diluted powder is able to be manufactured by such a manner that the present heterocyclic derivative (1) is made into an appropriate fine size and then mixed with a pharmaceutical carrier which is similarly made into the fine size such as edible carbohydrate (e.g., starch and mannitol). Flavoring agent, preservative, dispersing agent, coloring agent, perfume, etc. may be optionally added thereto.

Capsules are able to be manufactured by such a manner that the powder or diluted powder which is made powdery as mentioned above or granules which will be mentioned under the item for tablets is/are filled in an capsule shell such as gelatin capsule. It is also possible to manufacture in such a manner that the powder or the diluted powder in a powdery form is mixed with a lubricant or a fluidizing agent such as colloidal silica, talc, magnesium stearate, calcium stearate or solid polyethylene glycol followed by subjecting to a filling operation. When a disintegrating agent or solubilizing agent such as carboxymethyl cellulose, carboxymethyl cellulose calcium, lowly-substituted hydroxypropyl cellulose, croscarmellose sodium, carboxymethyl starch sodium, calcium carbonate or sodium carbonate is added, efficacy of the pharmaceutical when the capsules are ingested is able to be improved. It is also possible that fine powder of the present heterocyclic derivative (1) is suspended/dispersed in vegetable oil, polyethylene glycol, glycerol or surfactant and wrapped with a gelatin sheet to give a soft capsule preparation.

Tablets are able to be manufactured in such a manner that a powdery mixture is prepared by addition of a filler to the present heterocyclic derivative (1) which was made powdery and made into granules or slugs and then a disintegrating agent or a lubricant is added thereto followed by making into tablets.

The powdery mixture is able to be manufactured by mixing an appropriately powdered heterocyclic derivative (1) with a diluent or a base. If necessary, it is possible to add a binder (such as carboxymethyl cellulose sodium, methyl cellulose, hydroxypropyl methyl cellulose, gelatin, polyvinylpyrrolidone or polyvinyl alcohol), a dissolution retarding agent (such as paraffin), a reabsorbing agent (such as a quaternary salt), an adsorbent (such as bentonite or kaolin), etc. thereto.

The powdery mixture is able to be made into granules in such a manner that it is firstly made wet using a binder, for example, syrup, starch paste, acacia, cellulose solution or polymer solution, mixed with stirring and dried followed by grinding. Instead of making the powder into granules as such, it is also possible that the powder is applied to a tabletting machine and the resulting slug in an incomplete shape is ground to give granules. When a lubricant such as stearic acid, stearate, talc or mineral oil is added to the granules prepared as such, sticking of the granules each other is able to be prevented.

Tablets are also able to be manufactured in such a manner that the present heterocyclic derivative (1) is mixed with a fluid inert carrier and then directly making into tablets without conducting the above steps of making into granules or slugs.

The tablets prepared as such are able to be subjected to film coating or sugar coating. It is also possible to apply a transparent or semi-transparent protective coat comprising a tightly closed shellac film, a coat comprising sugar or polymer material, or a polished coat comprising wax.

In other oral preparation such as liquid, syrup, troche or elixir, it is also possible to make into a dose unit form where a predetermined amount thereof contains a predetermined amount of the present heterocyclic derivative (1).

The syrup is able to be manufactured by dissolving the present heterocyclic derivative (1) into an appropriate aqueous solution of flavor. The elixir is able to be manufactured using a non-toxic alcoholic carrier.

The suspension is able to be manufactured by dispersing the present heterocyclic derivative (1) into a non-toxic carrier. If necessary, it is possible to add a solubilizing agent or an emulsifier (such as ethoxylated isostearyl alcohol or polyoxyethylene sorbitol ester), a preservative or a flavor-endowing agent (such as peppermint oil or saccharine) thereto.

If necessary, the dose unit formulation for oral administration may be made into microcapsules. The formulation is also able to be coated or embedded into polymer or wax to obtain a prolonged action or sustained release of the active ingredient.

The parenteral preparation is able to be in a liquid dose unit form for subcutaneous, intramuscular or intravenous injection such as in a form of solution or suspension. The parenteral preparation is able to be manufactured in such a manner that a predetermined amount of the present heterocyclic derivative (1) is suspended or dissolved into a non-toxic liquid carrier meeting the purpose of injection such as aqueous or oily medium and then the suspension or solution is sterilized. Non-toxic salt or a solution thereof may be added thereto for making the injection solution isotonic. It is also possible to add a stabilizer, a preservative, an emulsifier and the like.

The suppository is able to be manufactured by dissolving or suspending the present heterocyclic derivative (1) into a low-melting and water-soluble or insoluble solid such as polyethylene glycol, cacao fat, semi-synthetic fat/oil (such as Witepsol (registered trade mark)), higher ester (such as myristyl palmitate) or a mixture thereof.

Although the dose of the agent for the treatment of inflammatory bowel diseases of the present invention may vary depending upon the state of a patient such as body weight or age, administering route or degree of symptom, a range of 0.001 mg to 100 mg/day as an amount of the present heterocyclic derivative (1) is generally suitable for an adult and a range of 0.01 mg to 10 mg is more preferable. In some cases, the dose less than the above may be sufficient or, on the other hand, the dose more than the above may be necessary. It is also possible to administer one to several times a day or to administer with an interval of one to several days.

EXAMPLES

The present invention will now be illustrated in more detail by way of the following test example although the present invention is not limited to the scope mentioned in the following range.

Test Example 1

(1) Methods

Rats (males; eight weeks age) of an F 334 strain (Japan SLC) were allowed free access to a 3% aqueous solution of dextran sulfate for five days and, after that, they were allowed free access to tap water for one day. The test substance was orally administered twice daily at the start of drinking of a 3% aqueous solution of dextran sulfate. After six days from the initiation of the administration, the large intestine was excised and its length was measured. With regard to the symptom score, (1) stool consistency, (2) fecal blood and (3) degree of body weight reduction from the previous day were evaluated in five stages as shown in the following Table 1 and a mean value thereof was calculated. As to the test substance, the compound A (5 mg/kg) was used. The test substance was administered by suspending in a 0.5% aqueous solution of methyl cellulose. A 0.5% aqueous solution of methyl cellulose was administered to the control group. Ten rats per group were used.

TABLE 1

| Symptom Score | Stool consistency | Fecal blood | Body Weight Reduction (ratio to previous day) |
|---|---|---|---|
| 0 | normal | nil | $<-1\%$ |
| 1 | a bit soft | light | $\geq -1\%$ and $<1\%$ |
| 2 | soft | medium | $\geq 1\%$ and $<3\%$ |
| 3 | a bit diarrhetic | heavy | $\geq 3\%$ and $<5\%$ |
| 4 | diarrhetic | melena | $\geq 5\%$ |

With regard to shortening of the large intestine, significant difference from the control group was tested by a t-test (*: $p<0.05$). With regard to the symptom score of colitis, significant difference from the control group was tested by a t-test (##: $p<0.01$).

(2) Results

Figure 2:
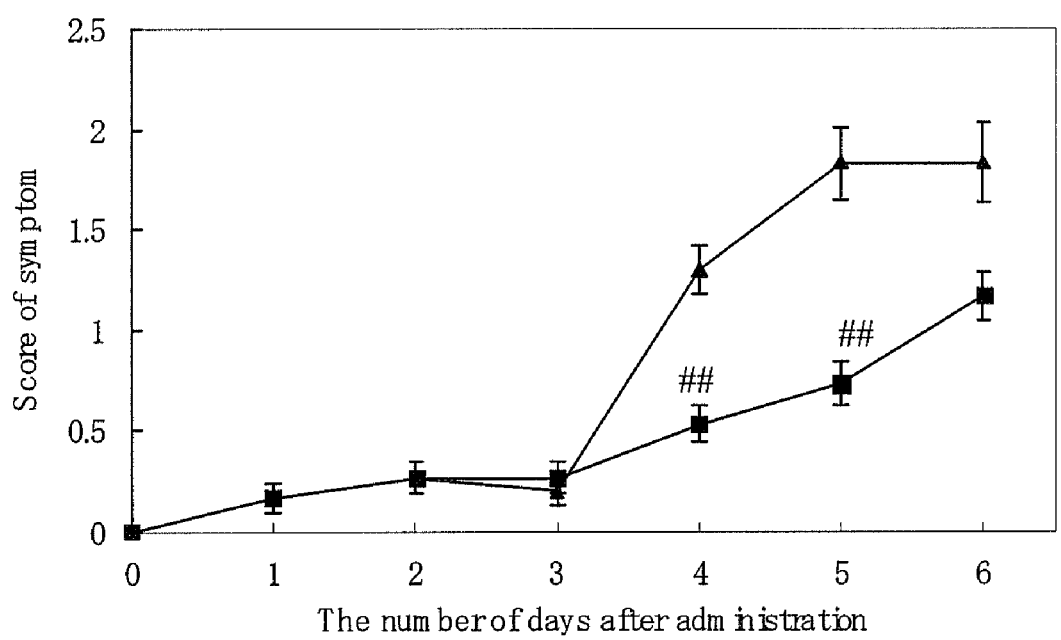
FIG. 2 shows changes in the symptom score of colitis. An ordinate represents the symptom score and an abscissa represents the numbers of days from initiation of free drinking of an aqueous solution of dextran sulfate.

As shown in FIG. 1, shortening of large intestine was significantly suppressed by administration of the compound A. As shown in FIG. 2, ingravescence of symptom of colitis was significantly suppressed by administration of the compound A.

Test Example 2

Rat is administered with trinitrobenzene sulfonic acid or acetic acid to cause colitis according to a previously described method (Gastroenterology 1992; 102: 1524-1534). Before or after administrating trinitrobenzene sulfonic acid or acetic acid, the rat is administered with the compound A or the compound B, and a change in mucosal permeability, colic histology or colic weight et al. is determined to evaluate the pharmacological effect of the compound A or the compound B.

Test Example 3

Rat is administered with dextran sulfate sodium to cause colitis according to a previously described method (Dig Dis Sci 2007; 52: 2095-2103). Before or after administrating dextran sulfate sodium, the rat is administered with the compound A or the compound B, and a change in mucosal $PGE_2$ content or an activity of myeloperoxidase et al. is determined to evaluate the pharmacological effect of the compound A or the compound B.

Test Example 4

Splenic cells derived from IL-10 deficient mouse were transplanted into SCID mouse to cause colitis according to a previously described method (Int Immunopharmacol 2005; 5: 993-1006). Thereafter, the mouse is administered with the compound A or the compound B, and a change in body weight or fecal consistency et al. is determined to evaluate the pharmacological effect of the compound A or the compound B.

Test Example 5

Rat is administered with trinitrobenzene sulfonic acid or acetic acid to cause colitis according to a previously described method (Jpn Pharmacol Ther 2008; 36: 293-301). Before or after administrating trinitrobenzene sulfonic acid or acetic acid, the rat is administered with the compound A or the compound B, and a change in active oxygen or leukotriene B4 content et al. is determined to evaluate the pharmacological effect of the compound A or the compound B.

The invention claimed is:

1. A method for treating inflammatory bowel disease in a patient comprising administering to the patient a pharmaceutical composition comprising 2-{4-[N-(5,6-diphenylpyrazin-2-yl)-N-isopropylamino]butyloxy}acetic acid or 2-{4-[N-(5,6-diphenylpyrazin-2-yl)-N-isopropylamino]butyloxy}-N-(methylsulfony)acetamide, or a pharmaceutically acceptable salt thereof.

2. The method of claim 1, wherein the inflammatory bowel disease is ulcerative colitis, Crohn's disease, intestinal tuberculosis, ischemic colitis or intestinal ulcer associated with Behcet disease.

* * * * *